US009192615B2

(12) United States Patent
Wortzman et al.

(10) Patent No.: US 9,192,615 B2
(45) Date of Patent: Nov. 24, 2015

(54) METHOD FOR THE TREATMENT OF ACNE AND CERTAIN DOSAGE FORMS THEREOF (75) Inventors: Mitchell Wortzman, Scottsdale, AZ (US); R. Todd Plott, Dallas, TX (US); Steven B. Newhard, Scottsdale, AZ (US); David Watt, Pickering (CA)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 834 days.

(21) Appl. No.: 12/536,359

(22) Filed: Aug. 5, 2009

(65) Prior Publication Data
US 2010/0035846 A1    Feb. 11, 2010

Related U.S. Application Data (60) Provisional application No. 61/086,728, filed on Aug. 6, 2008, provisional application No. 61/210,882, filed on Mar. 23, 2009.

(51) Int. Cl.
*A61K 31/65* (2006.01)
*A61K 9/20* (2006.01)

(52) U.S. Cl.
CPC ............... *A61K 31/65* (2013.01); *A61K 9/2018* (2013.01); *A61K 9/2054* (2013.01)

(58) Field of Classification Search
CPC .... A61K 31/65; A61K 9/2018; A61K 9/2054
See application file for complete search history.

(56) References Cited

U.S. PATENT DOCUMENTS

| | | |
|---|---|---|
| 2,420,708 A | 5/1947 | Hutsell |
| 3,932,615 A | 1/1976 | Ito et al. |
| 3,957,980 A | 5/1976 | Noseworthy |
| 3,966,922 A | 6/1976 | Okamoto et al. |
| 4,086,332 A | 4/1978 | Armstrong |
| 4,126,680 A | 11/1978 | Armstrong |
| 4,138,475 A | 2/1979 | McAinsh et al. ............... 424/19 |
| 4,369,172 A | 1/1983 | Schor et al. |
| 4,376,118 A | 3/1983 | Daher et al. |
| 4,443,442 A | 4/1984 | Skillern |
| 4,701,320 A | 10/1987 | Hasegawa et al. |
| 4,764,377 A | 8/1988 | Goodson |
| 4,792,448 A | 12/1988 | Ranade |
| 4,806,529 A | 2/1989 | Levy |
| 4,837,030 A * | 6/1989 | Valorose et al. ............... 424/456 |
| 4,925,833 A | 5/1990 | McNamara et al. |
| 4,935,411 A | 6/1990 | McNamara et al. |
| 4,935,412 A | 6/1990 | McNamara et al. |
| 4,960,913 A | 10/1990 | Szalay et al. |
| 5,007,790 A | 4/1991 | Shell |
| 5,009,895 A * | 4/1991 | Lui ............... 424/465 |
| 5,122,519 A | 6/1992 | Ritter |
| 5,167,964 A | 12/1992 | Muhammad et al. |
| 5,188,836 A | 2/1993 | Muhammad et al. |
| 5,202,128 A | 4/1993 | Morella et al. |
| 5,209,978 A | 5/1993 | Kosaka et al. |
| 5,211,958 A | 5/1993 | Akkerboom et al. |
| 5,217,493 A | 6/1993 | Raad et al. |
| 5,230,895 A | 7/1993 | Czarnecki et al. |
| 5,262,173 A | 11/1993 | Sheth et al. |
| 5,277,916 A | 1/1994 | Dwyer et al. |
| 5,283,065 A | 2/1994 | Doyon et al. |
| 5,300,304 A | 4/1994 | Sheth et al. .................. 424/490 |
| 5,324,751 A | 6/1994 | DuRoss |
| 5,348,748 A | 9/1994 | Sheth et al. |
| 5,413,777 A | 5/1995 | Sheth et al. |
| 5,459,135 A | 10/1995 | Golub et al. |
| 5,518,730 A | 5/1996 | Fuisz |
| 5,554,654 A | 9/1996 | Yu et al. |
| 5,582,837 A | 12/1996 | Shell |
| 5,665,776 A | 9/1997 | Yu et al. |
| 5,674,539 A | 10/1997 | Tomas |
| 5,698,593 A | 12/1997 | Peck |
| 5,776,489 A | 7/1998 | Preston et al. |
| 5,780,049 A | 7/1998 | Deckner et al. |
| 5,783,212 A | 7/1998 | Fassihi et al. |
| 5,789,395 A | 8/1998 | Amin et al. |
| 5,800,836 A | 9/1998 | Morella et al. |

(Continued)

FOREIGN PATENT DOCUMENTS

| | | |
|---|---|---|
| CA | 2025703 A1 | 3/1991 |
| CA | 2068366 A1 | 11/1992 |

(Continued)

OTHER PUBLICATIONS

Methocel E50 Premium LV at www.dow.com/personalcare/technologies/rheology/methocel.htm (retrieved from the internet Dec. 4, 2014).*
Fanning, et al., "Distressing Side-Effects of Minocycline Hydrochloride," Arch. Intern. Med., vol. 136, pp. 761-762 (1976).
Gould, et al., "Minocycline Therapy," Arch. Otolaryngol., vol. 96, p. 291 (1972).
Leyden, J., "New Extended-Release Minocycline—First Systemic Antibiotic Approved for the Treatment of Acne," Cutis vol. 78 (suppl. 4):4-5 (2006).
Shah, et al., "In vitro Dissolution Profile Comparison—Statistics and Analysis of the Similarity Factor, f2," Pharmaceutical Research, vol. 15, No. 6, pp. 889-896, 1998.
Stewart, M., et al., "Dose-Ranging Efficacy of new Once-Daily Extended-Release Minocycline for Acne Vulgaris," Cutis vol. 78 (suppl. 4):11-20 (2006).
Williams et al., "Minocycline: Possible Vestibular Side Effects," Lancet, pp. 144-145, (Sep. 28, 1974).
Notification of Transmittal of International Preliminary Report on Patentbility dated Oct. 4, 2010 for corresponding International Patent Application No. PCT/US2009/052873.

(Continued)

*Primary Examiner* — Dennis Heyer
(74) *Attorney, Agent, or Firm* — John E. Thomas, Esq.; Harter Secrest & Emery LLP (57) ABSTRACT An oral dosage form, including 65 mg of minocycline, an amount of lactose monohydrate, and an amount of hydroxypropylmethylcellulose. The hydroxypropylmethylcellulose is hydroxypropylmethylcellulose that is about 8.9+/−0.2% hydroxypropoxylated. An oral dosage form, including 115 mg of minocycline, an amount of lactose monohydrate, and an amount of hydroxypropylmethylcellulose. The hydroxypropylmethylcellulose is hydroxypropylmethylcellulose that is about 8.9+/−0.2% hydroxypropoxylated.

4 Claims, 5 Drawing Sheets

(56) References Cited

U.S. PATENT DOCUMENTS

| | | |
|---|---|---|
| 5,814,331 A | 9/1998 | Holen |
| 5,824,343 A | 10/1998 | Ng et al. |
| 5,834,450 A | 11/1998 | Su |
| 5,855,904 A | 1/1999 | Chung et al. |
| 5,908,838 A | 6/1999 | Gans |
| 5,972,389 A | 10/1999 | Shell et al. |
| 6,015,804 A | 1/2000 | Golub et al. |
| 6,087,382 A | 7/2000 | Bonner, Jr. et al. |
| 6,120,803 A | 9/2000 | Wong et al. |
| 6,165,513 A | 12/2000 | Dansereau et al. |
| 6,165,999 A | 12/2000 | Vu |
| 6,194,000 B1 | 2/2001 | Smith et al. |
| 6,340,475 B2 | 1/2002 | Shell et al. |
| 6,340,476 B1 | 1/2002 | Midha et al. |
| 6,429,204 B1 | 8/2002 | Golub et al. |
| 6,455,583 B1 | 9/2002 | Pflugfelder et al. |
| 6,497,902 B1 | 12/2002 | Ma |
| 6,585,997 B2 | 7/2003 | Moro et al. |
| 6,638,922 B2 | 10/2003 | Ashley et al. |
| 6,667,060 B1 | 12/2003 | Vandecruys et al. |
| 6,673,843 B2 | 1/2004 | Arbiser |
| 6,863,830 B1 | 3/2005 | Purdy et al. |
| 6,958,161 B2 | 10/2005 | Hayes et al. |
| 7,008,631 B2 | 3/2006 | Ashley |
| 7,063,862 B2 | 6/2006 | Lin et al. |
| 7,211,267 B2 | 5/2007 | Ashley |
| 7,541,347 B2 | 6/2009 | Wortzman et al. |
| 7,544,373 B2 | 6/2009 | Wortzman et al. |
| 7,790,705 B2 | 9/2010 | Wortzman et al. |
| 7,919,483 B2 | 4/2011 | Wortzman et al. |
| 7,976,870 B2 | 7/2011 | Berner et al. |
| 8,722,650 B1 | 5/2014 | Wortzman et al. |
| 2002/0015731 A1 | 2/2002 | Appel et al. |
| 2002/0044968 A1 | 4/2002 | van Lengerich |
| 2003/0044446 A1 | 3/2003 | Moro et al. |
| 2003/0082120 A1 | 5/2003 | Milstein |
| 2003/0130240 A1 | 7/2003 | Ashley |
| 2003/0139380 A1 | 7/2003 | Ashley |
| 2003/0199480 A1 | 10/2003 | Hayes et al. |
| 2003/0229055 A1 | 12/2003 | Ashley |
| 2004/0002481 A1 | 1/2004 | Ashley et al. |
| 2004/0037789 A1 | 2/2004 | Moneuze et al. |
| 2004/0115261 A1 | 6/2004 | Ashley |
| 2004/0127471 A1 | 7/2004 | Reisberg |
| 2004/0185105 A1 | 9/2004 | Berner et al. |
| 2004/0228912 A1 | 11/2004 | Chang et al. |
| 2005/0136107 A1 | 6/2005 | Patel et al. |
| 2005/0148552 A1 | 7/2005 | Ryan et al. |
| 2006/0293290 A1* | 12/2006 | Wortzman et al. ............ 514/152 |
| 2007/0154547 A1 | 7/2007 | Flanner et al. |
| 2007/0254855 A1 | 11/2007 | Wortzman et al. |
| 2007/0259039 A1 | 11/2007 | Wortzman et al. |
| 2007/0270390 A1 | 11/2007 | Wortzman et al. |
| 2007/0275933 A1 | 11/2007 | Wortzman et al. |
| 2008/0070872 A1 | 3/2008 | Wortzman et al. |
| 2008/0161273 A1 | 7/2008 | Arsonnaud et al. |
| 2008/0241197 A1* | 10/2008 | Wortzman et al. ............ 424/400 |
| 2008/0241235 A1* | 10/2008 | Wortzman et al. ............ 424/465 |
| 2008/0241236 A1* | 10/2008 | Wortzman et al. ............ 424/465 |
| 2008/0241241 A1* | 10/2008 | Wortzman et al. ............ 424/472 |
| 2008/0242641 A1* | 10/2008 | Wortzman et al. ............ 514/152 |
| 2008/0242642 A1* | 10/2008 | Wortzman et al. ............ 514/152 |
| 2008/0260824 A1 | 10/2008 | Nangia et al. |
| 2008/0318910 A1 | 12/2008 | Desjardins et al. |
| 2010/0215744 A1 | 8/2010 | Watt et al. |
| 2010/0330131 A1 | 12/2010 | Wortzman et al. |

FOREIGN PATENT DOCUMENTS

| | | |
|---|---|---|
| CA | 2090561 A1 | 9/1993 |
| CN | 101658501 A | 3/2010 |
| CN | 101822650 A | 9/2010 |
| EP | 0184389 A2 | 6/1986 |
| EP | 0418565 A2 | 3/1991 |
| EP | 0558913 A1 | 9/1993 |
| GB | 2414668 A | 12/2005 |
| JP | H026437 A | 1/1990 |
| WO | WO-9318755 A1 | 9/1993 |
| WO | WO-9811879 A1 | 3/1998 |
| WO | WO-9855107 A1 | 12/1998 |
| WO | WO-9958131 A1 | 11/1999 |
| WO | WO-02080932 A1 | 10/2002 |
| WO | WO-03088906 A2 | 10/2003 |
| WO | WO-2004012700 A2 | 2/2004 |
| WO | WO-2004078111 A2 | 9/2004 |
| WO | WO-2004091483 A2 | 10/2004 |
| WO | WO-2007038867 A1 | 4/2007 |
| WO | WO-2007102447 A1 | 9/2007 |
| WO | WO-2008102161 A2 | 8/2008 |

OTHER PUBLICATIONS

Notification of Transmittal of International Preliminary Report on Patentbility dated Oct. 4, 2010 for corresponding International Patent Application No. PCT/US2009/052873 (previously submitted on Oct. 25, 2010).

International Search Report and Written Opinion dated Oct. 1, 2009 for corresponding International patent application No. PCT/US2009/052873.

"A Comparison of the Side Effects Produced by Vectrin and Dynacin After Normal Dosage," Clinical Acne Reviews vol. 2, (1977).

AAI International Procore.RTM. Technology, referencing patents issued prior to 2000.

AAI International PROSLOTM and PROSLOTM II Tablets Technology, referencing patents issued prior to 2000.

Gupta, A.K. et al., "Solodyn (Minocycline HCI, USP) Extended-Release Tablets," LE JACQ, 291-292, Nov. Dec. 2006.

Agwuh, K.N. and MacGowan, A., "Pharmacokinetics and pharmacodynamics of the tetracyclines including glycylcyclines," Journal of Antimicrobial Chemotherapy 58(2):256-265, Oxford University Press, England (2006).

Darrah, AJ., et al., "An open multicentre study to compare fusidic acid lotion and oral minocycline in the treatment of mild-to-moderate acne vulgaris of the face," European Journal of Clinical Research 8:97-107, (1996).

Akamatsu, H., et al., "Effect of doxycycline on the generation of reactive oxygen species: a possible mechanism of action of acne therapy with doxycycline," Acta Dermato-Venereologica 72(3):178-179, Society for the Publication of Acta Dermato-Venereologica, Sweden (1992).

Akamatsu, H., et al., "Effects of subminimal inhibitory concentrations of minocycline on neutrophil chemotactic factor production in comedonal bacteria, neutrophil phagocytosis and oxygen metabolism," Archives of Dermatological Research 283(8):524-528, American Medical Assn, United States (1991).

American Hospital Formulary Service, AHFS Drug Information, 446-448, (2003).

American Hospital Formulary Service Drug Information 88, pp. 330-331, (1988).

Anlar, S., et al., "Physico-chemical and bioadhesive properties of polyacrylic acid polymers," Die Pharmazie 48(4):285-287, Govi-Verlag Pharmazautischer Verlag, Germany (1993).

Arndt., et al., "What disorders present with inflamed skin?Cutaneous Medicine and Surgery," An Integrated Program in Dermatology 1:470-471, (1996).

Arnold, H.L., et al., "Andrews' Diseases of the Skin: Clinical Dermatology," Edition 8:254, (1990).

Bikowski, J.B., et al., "Treatment of rosacea with doxycycline monohydrate," Cutis 66(2):149-152, Quadrant HealthCom, United States (2000).

Dreno, B., "Multicenter Randomized Comparative Double-Blind Controlled Clinical Trail of the Safety and Efficacy of Zinc Gluconate versus Minocycline Hydrochloride in the Treatment of Inflammatory Acne vulgaris," Dermatology 203:135-140, Karger, Switzerland (2001).

Brown, S.I. and Shahinian, L, Jr., "Diagnosis and treatment of ocular rosacea," Ophthalmology 85(8):779-786, American Academy of Ophthalmology, United States (1978).

(56) References Cited

OTHER PUBLICATIONS

"Carbopol and its Applications in pharmaceutical dosage forms," accessed at www.pharmainfo.net, accessed on Sep. 27, 2007, 6 pages.

"Carbopol Polymers for Pharmaceutical Drug Delivery applications", accessed at www.drugdeliverytech.com/ME2/dimrod.asp, accessed on Jun. 2003, 3 pages.

Cartwright, A.C., et al., "A comparison of the bioavailability of minocycline capsules and film-coated tablets," Journal of Antimicrobial Chemotherapy 1(3):317-322, Oxford University Press, England (1975).

Champion, R.H., et al., ed. "Disorders of the Sebaceous Glands," Textbook of Dermatology, Edition 6,vol. 3, 1958-1961 (1998).

Cohen, P.M. "A general practice study investigating the effect of Minocin 50 mg b.d. for 12 weeks in the treatment of acne vulgaris," Journal of International Medical Research 13(4):214-221, Sage Publications, England (1985).

Coskey, R.J. "Acne: treatment with minocycline," Cutis 17(4):799-801, Quadrant HealthCom, United States (1976).

Cullen, S.I. and Cohan, R.H., "Minocycline therapy in acne vulgaris," Cutis 17(6):1208-1210, Quadrant HealthCom, United States (1976).

Cullen, S.I. "Low-dose minocycline therapy in tetracycline-recalcitrant acne vulgaris," Cutis 21(1):101-104, Quadrant HealthCom, United States (1978).

De Paz, S., et al., "Severe hypersensitivity reaction to minocycline," Journal of Investigational Allergology and Clinical Immunology 9(6):403-404, Esmon Publicidad, Spain (1999).

Del Rosso, J.Q. "A status report on the use of subantimicrobial-dose doxycycline: a review of the biologic and antimicrobial effects of the tetracyclines," Cutis 74(2):118-122, Quadrant HealthCom, United States (2004).

Del Rosso, J.Q. "Recently approved systemic therapies for acne vulgaris and rosacea," Cutis 80(2):113-120, Quadrant HealthCom, United States (2007).

Del Rosso, J.Q. "Clinical significance of brand versus generic formulations: focus on oral minocycline," 77(3):153-156, (2006).

Del Rosso, J.Q. and Kim, G., "Optimizing use of oral antibiotics in acne vulgaris," Dermatologic Clinics 27(1):33-42, Elsevier Science, United States (2009).

Del Rosso, J.Q., et al., "Current approach to acne management: a community-based analysis," Cutis 83(6 Suppl):5-21, Quadrant HealthCom, United States (2009).

Del Rosso, J.Q., "What's new in the Medicine Cabinet?," Skin and Aging Conference :3-6, (2005).

Drugs.com , Drug information online, Minocin PAC product information, Aug. 2007.

Eady, A.E., et al., "Is antibiotic resistance in cutaneous propionibacteria clinically relevant? : implications of resistance for acne patients and prescribers," American Journal of Clinical Dermatology 4(12):813-831, (2003).

Fernandez-Obregon, A.C., "Azithromycin for the treatment of acne," International Journal of Dermatology 39(1):45-50, Blackwell Publishing, England (2000).

Fingleton, B., "CMT-3 CollaGenex," Current Opinion in Investigational Drugs 4(12):1460-1467, PharmaPress Ltd in association with Current Drugs Ltd, England (2003).

Fleischer, A.B. Jr., "Safety and efficacy of a new extended-release formulation of minocycline," Cutis 78(4 Suppl):21-31, Quadrant HealthCom, United States (2006).

Freedberg, I.M, et al., ed. "Fizpatrick's Dermatology in General Medicine," Edition 5:777-778, (1999).

Freeman.K. "Therapeutic focus, Minocycline in the treatment of acne," British Journal of Clinical Pharmacology, 43(3):112-115, Harvey & Blythe Ltd, England (1989).

Gans, E. and Higuchi, T., "The solubility and complexing properties of oxytetracycline and tetracycline. II. Interactions in Nonaqueous solution," Journal of American Pharmacists Association 46(10):587-591, American Pharmaceutical Association, United States (1957).

Gardner, K.J., et al., "Comparison of serum antibiotic levels in acne patients receiving the standard or a modified release formulation of minocycline hydrochloride," Clinical and Experimental Dermatology 22(2):72-76, Blackwell Scientific Publications, England (1997).

Garner S.E., et al., "Minocycline for acne vulgaris: efficacy and safety," The Cochrane Library 1:, John Wiley & Sons, United Kingdom, http://212.49.218.203/newgenMB/ASP/printDocument.asp, Apr. 14, 2004.

Gilbert, RD and Plott, RT, "Extended-Release Minocycline: Is Efficacy Dose-dependent in the Approved Dose Range?," Poster Presentation for the Dusa Pharmaceuticals, Inc , 3-9, (2007).

Goldstein, N.S., et al., "Minocycline as a cause of drug-induced autoimmune hepatitis. Report of four cases and comparison with autoimmune hepatitis," 114(4):591-598 American Society of Clinical Pathologists, United States (2000).

Gollnick, H., et al., "Management of acne: a report from a Global Alliance to Improve Outcomes in Acne," Journal of the American Academy of Dermatology 49(1 Suppl):S1-537, Elsevier Science, United States (2003).

Golub, L.M., et al., "Tetracyclines inhibit connective tissue breakdown: new therapeutic implications for an old family of drugs," Critical Reviews in Oral Biology & Medicine 2(3):297-321, International Association for Dental Research, United States (1991).

Gump, D.W., et al., "Side effects of minocycline: different dosage regimens," Antimicrobial Agents and Chemotherapy 12(5):642-646, American Society for Microbiology, United States (1977).

Harrison, P.V., et al., "A comparison of doxycycline and minocycline in the treatment of acne vulgaris," Clinical and Experimental Dermatology 13(4):242-244, Blackwell Scientific Publications, England (1988).

Healy, E. and Simpson, N., "Acne vulgaris," British Medical Journal 308(6932):831-833, British Medical Association, England (1994).

Hersle, K. and Gisslen, H., "Minocycline in acne vulgaris: a double-blind study," Current Therapeutic Research 19(3):339-342, Therapeutic Research Press, Inc., United States (1976).

Hubbell, C.G., et al., "Efficacy of minocycline compared with tetracycline in treatment of acne vulgaris," Archives of Dermatological Research 118(12):989-992, American Medical Assn, United States (1982).

Illig.L. "Positive Side Effects of Antibiotic and Antimicrobial Substances in Therapy," Infection 7(6):5584-5588.

International Search Report and Written Opinion for International Application No. PCT/US06/23761, mailed on Feb. 26, 2007.

"Is minocycline overused in acne?," Drug Ther Bull 44(8):60-62, the BMJ Publishing Group Ltd, England (2006).

Islam, M.M., et al., "A nonantibiotic chemically modified tetracycline (CMT-3) inhibits intimal thickening," American Journal of Pathology 163(4):1557-1566, Elsevier Science, United States (2003).

Del Rosso., J.Q. et al. "Weight-based Dosing of a Novel Antibiotic for Moderate-to-Severe Acne Vulgaris Offers Potential for Improved Safety and Tolerability," www.millennium.com/go/acne, Millennium CME Institute, Inc., (2006).

Johnson, B.A. and Nunley, J.R., "Use of systemic agents in the treatment of acne vulgaris," American Family Physician 62(8):1823-1830, 1835-1836, American Academy of Family Physicians, United States (2000).

Jonas, M. and Cunha, B.A., "Minocycline," Therapeutic Drug Monitoring 4(2):137-145, Lippincott Williams & Wilkins, United States (1982).

Kelly, R.G. and Kanegis, L.A., "Metabolism and tissue distribution of radioisotopically labelled minocycline," Toxicology and Applied Pharmacology 11(1):171-183, Academic Press, United States (1967).

Lawrenson, R.A., et al., "Liver damage associated with minocycline use in acne: a systematic review of the published literature and pharmacovigilance data," Drug Safety 23(4):333-349, ADIS Press Limited, New Zealand (2000).

Leyden, J., et al., "Comparison of tazarotene and minocycline maintenance therapies in acne vulgaris: a multicenter, double-blind, randomized, parallel-group study," Archives of Dermatological Research 142(5):605-612, American Medical Association, United States (2006).

(56) References Cited

OTHER PUBLICATIONS

Leyden, J. "Introduction," Cutis 78 (suppl 4):4-5, Quadrant HealthCom, United States (2006).
Leyden, J.J., et al., "Absorption of minocycline hydrochloride and tetracycline hydrochloride. Effect of food, milk, and iron," Journal of the American Academy of Dermatology 12(2 Pt 1):308-312, Elsevier Science, United States (1985).
Leyden, J.J., et al., "Clinical considerations in the treatment of acne vulgaris and other inflammatory skin disorders: focus on antibiotic resistance," Cutis 79(6 Suppl):9-25, Quadrant HealthCom, United States (2007).
Leyden, J.J., et al., "Pseudomonas aeruginosa gram-negative folliculitis," Archives of Dermatological Research 115(10):1203-1204, American Medical Association, United States (1979).
Leyden, J.J., et al., "Tetracycline and minocycline treatment," Archives of Dermatological Research 118(1):19-22, American Medical Association, United States (1982).
Leyden.,et al., "The antimicrobial effects in vivo of minocycline, doxycycline and tetracycline in humans," The Journal of Dermatological Treatment 7:223-225, Informa Healthcare, England (1996).
Li, J., et al., "Evidence for dissolution rate-limited absorption of COL-3, a matrix metalloproteinase inhibitor, leading to the irregular absorption profile in rats after oral administration," Pharmaceutical Research 19(11):1655-1662, Kluwer Academic/Plenum Publishers, United States (2002).
Lokeshwar, B.L., et al., "Inhibition of cell proliferation, invasion, tumor growth and metastasis by an oral non-antimicrobial tetracycline analog (Col-3) in a metastatic prostate cancer model," International Journal of Cancer 98(2):297-309, Wiley-Liss, United States (2002).
Lubrizol Pharmaceutical Bulletin 23, Oct. 29, 2008, Bioadhesion (Lubrizol Advanced Materials, Inc.), consisting of 20 pages.
MacDonald, H., et al., "Pharmacokinetic studies on minocycline in man," Clinical pharmacology and therapeutics 14(5):852-861, Wiley, United States (1973).
Mahaguna, V., et al., "Influence of hydroxypropyl methylcellulose polymer on in vitro and in vivo performance of controlled release tablets containing alprazolam," European Journal of Pharmaceutics and Biopharmaceutics 56(3):461-468, Elsevier Science, Netherlands (2003).
Marks, R., et al., (eds.) "Dermatologic Therapy in Current Practice", Chapter 3, 35-44, (2002).
Millar, E.D., et al., "A general practice study investigating the effect of minocycline (Minocin) 50 mg bd for 12 weeks in the treatment of acne vulgaris," The British journal of clinical practice 41(8):882-886, Medicom International, England (1987).
Minocin Product Insert, Wyeth Pharmaceuticals Inc. Rev Oct. 2005, 16 pages.
Minocycline Hydrochloride Capsules, USP Bioequivalence Study, 9 pages.
MinoPAC product information, Monthly prescribing Reference (Oct. 2006) and the product information (Aug. 2007).
Nayak., et al., "Gastroretentive drug delivery systems: a review," Asian Journal of Pharmaceutical and Clinical Research 3(1):2-10, Elsevier Science, United States (2010).
Ochsendorf, F., "Systemic antibiotic therapy of acne vulgaris," Journal der Deutschen Dermatologischen Gesellschaft 4(10):828-841, Blackwell, Germany (2006).
Office Action mailed Apr. 2, 2010, in U.S. Appl. No. 11/944,186, Mitchell Wortzman., et al., filed Nov. 21, 2007.
Office Action mailed Aug. 8, 2008, in U.S. Appl. No. 11/776,676, Mitchell Wortzman., et al., filed Jul. 12, 2007.
Office Action mailed Dec. 1, 2008, in U.S. Appl. No. 11/776,669, Mitchell Wortzman., et al., filed Jul. 12, 2007.
Office Action mailed Dec. 23, 2008, in U.S. Appl. No. 11/695,539, inventors Mitchell Wortzman., et al., filed Apr. 2, 2007.
Office Action mailed Dec. 24, 2008, in U.S. Appl. No. 11/695,514, Mitchell Wortzman., et al., filed Apr. 2, 2007.
Office Action mailed Jul. 22, 2008, in U.S. Appl. No. 11/695,528, inventors Mitchell Wortzman., et al., filed Apr. 2, 2007.
Office Action mailed Jul. 23, 2008, in U.S. Appl. No. 11/695,539, inventors Mitchell Wortzman., et al., filed Apr. 2, 2007.
Office Action mailed Jun. 10, 2009, in U.S. Appl. No. 11/695,514, Mitchell Wortzman., et al., filed Apr. 2, 2007.
Office Action mailed Jun. 10, 2009, in U.S. Appl. No. 11/776,676, Mitchell Wortzman., et al., filed Jul. 12, 2007.
Office Action mailed Jun. 17, 2008, in U.S. Appl. No. 11/776,669, Mitchell Wortzman., et al., filed Jul. 12, 2007.
Office Action mailed Jun. 17, 2008, in U.S. Appl. No. 11/776,711, Mitchell Wortzman., et al., filed Jul. 12, 2007.
Office Action mailed Jun. 25, 2009, in U.S. Appl. No. 11/776,669, Mitchell Wortzman., et al., filed Jul. 12, 2007.
Office Action mailed Mar. 4, 2010, in in U.S. Appl. No. 12/253,845, inventors Mitchell Wortzman., et al., filed Oct. 17, 2008.
Office Action mailed Mar. 31, 2010, in U.S. Appl. No. 11/776,669, Mitchell Wortzman., et al., filed Jul. 12, 2007.
Office Action mailed Mar. 31, 2010, in U.S. Appl. No. 11/776,676, Mitchell Wortzman., et al., filed Jul. 12, 2007.
Office Action mailed Mar. 31, 2010, in U.S. Appl. No. 11/776,711, Mitchell Wortzman., et al., filed Jul. 12, 2007.
Office Action mailed May 29, 2009, in U.S. Appl. No. 11/776,711, Mitchell Wortzman., et al., filed Jul. 12, 2007.
Office Action mailed May 29, 2009, in U.S. Appl. No. 11/944,186, Mitchell Wortzman., et al., filed Nov. 21, 2007.
Office Action mailed Nov. 6, 2007, in U.S. Appl. No. 11/166,817, inventors Mitchell Wortzman., et al., filed Jun. 24, 2005.
Office Action mailed Nov. 6, 2007, in U.S. Appl. No. 11/776,669, Mitchell Wortzman., et al., filed Jul. 12, 2007.
Office Action mailed Nov. 6, 2007, in U.S. Appl. No. 11/776,676, Mitchell Wortzman., et al., filed Jul. 12, 2007.
Office Action mailed Nov. 6, 2007, in U.S. Appl. No. 11/776,711, Wortzman, M., et al., filed Jul. 12, 2007.
Office Action mailed Nov. 13, 2008, in U.S. Appl. No. 11/166,817, inventors Mitchell Wortzman., et al., filed Jun. 24, 2005.
Office Action mailed Nov. 17, 2008, in U.S. Appl. No. 11/944,186, Mitchell Wortzman., et al., filed Nov. 21, 2007.
Office Action mailed Nov. 17, 2009, in in U.S. Appl. No. 12/253,845, inventors Mitchell Wortzman., et al., filed Oct. 17, 2008.
Office Action mailed Oct. 18, 2011, in U.S. Appl. No. 12/536,359, inventors Mitchell Wortzman., et al., filed Aug. 5, 2009.
Office Communication mailed Nov. 6, 2007, in Chinese Patent Application No. 2006800224203 (with English translation).
Opadry II Brochure, 1990, consisting of 3 pages.
Physician's Desk Reference, 43rd Edition ., MINOCINO: Minocycline Hydrochloride for Oral Use, , pp. 1134-1136, Edward R. Barnhard, publisher, Medical Economics Co., Inc., Oradell, NJ(1989).
Physician's Desk Reference, RTM., 51st Ed., Minocin.RTM. Minocycline Hydrochloride Pellet-Filled Capsules, pp. 1429-1431, Thomson PDR, Montvale, NJ (1997).
Piérard-Franchimont, C., et al., "Lymecycline and minocycline in inflammatory acne: a randomized, double-blind intent-to-treat study on clinical and in vivo antibacterial efficacy," Skin Pharmacology and Applied Skin Physiology 15(2):112-119, Karger AG, Switzerland (2002).
Plott, R.T. and Wortzman, M.S., "Key bioavailability features of a new extended-release formulation of minocycline hydrochloride tablets," Cutis 78(4 Suppl):6-10, Quadrant HealthCom, United States (2006).
Prescribingreference.com, Prescribing Reference, Drug News—Minocin PAC for Acne , Oct. 11, 2006.
Sapadin, A.N. and Fleischmajer, R., "Tetracyclines: nonantibiotic properties and their clinical implications," Journal of the American Academy of Dermatology 54(2):258-265, Elsevier Science, United States (2006).
Schach Von Wittenau, M. and Delahunt, C.S., "The distribution of tetracyclines in tissues of dogs after repeated oral administration," Journal of Pharmacology and Experimental Therapeutics 152(1):164-169, the American Society for Pharmacology and Experimental Therapeutics, United States (1966).

(56) References Cited

OTHER PUBLICATIONS

Seftor, R.E., et al., "Chemically modified tetracyclines inhibit human melanoma cell invasion and metastasis," Clinical and Experimental Metastasis 16(3):217-225, Kluwer Academic Publishers, Netherlands (1998).

Shalita, A. "The integral role of topical and oral retinoids in the early treatment of acne," Journal of the European Academy of Dermatology and Venereology 15(Suppl 3):43-49, Blackwell Publishing, United States (2001).

Sheehan-Dare, R.A., et al., "A double-blind comparison of topical clindamycin and oral minocycline in the treatment of acne vulgaris," Acta Dermato-Venereologica 70(6):534-537, Society for the Publication of Acta Dermato-Venereologica, Sweden (1990).

Smit, F., "Minocycline versus doxycycline in the treatment of acne vulgaris. A double-blind study," Dermatologica 157(3):186-190, Karger, Switzerland (1978).

Smith, K. and Leyden, J.J., "Safety of doxycycline and minocycline: a systematic review," Clinical Therapeutics 27(9):1329-1342, Elsevier Science, United States (2005).

Solodyn (Minocycline HC1 Extended Release Tablets) Labeling and package insert information, submitted with a New Drug Application approved May 8, 2006.

TA, C.N., et al., "Effects of minocycline on the ocular flora of patients with acne rosacea or seborrheic blepharitis," Cornea 22(6):545-548, Lippincott Williams & Wilkins, United States (2003).

Torok, et al., "Long-Term Safety of a Modified-Release Formulation of Minocycline for Treating Moderate to Severe Acne," program and abstracts of the Foundation of Research and Education in Dermatology Winter Clinical Dermatology Conference, Mar. 14-18, 2008, Kapalua, Hawaii, 9 pages.

Webster, G.F., et al., "Inflammation in acne vulgaris," Journal of the American Academy of Dermatology 33(2 Pt 1):247-253, Elsevier Science, United States (1995).

Webster, G.F., et al., "Suppression of polymorphonuclear leukocyte chemotactic factor production in Propionibacterium acnes by subminimal inhibitory concentrations of tetracycline, ampicillin, minocycline, and erythromycin," Antimicrobial Agents and Chemotherapy 21(5):770-772, American Society for Microbiology, United States (1982).

Yang, Jian, et al., LingNan Skin Disease Magazine, No. 1, pp. 38 (1994) (with English translation).

\* cited by examiner

Extragranular Adjustment Calculation and Batch History - Solodyn 65 and 115 mg ER Tablets

Intragranular Yield Calculation

Yield = (Total Net Weight x 100) ÷ Theoretical Weight

Yield = (Total Net Weight x 100) ÷ 166.25 kg = _____ ÷ 166.25 = _____ %

Quantity of Magnesium Stearate, #2255

Quantity of Magnesium Stearate, #2255 = (2.850 x % yield ) ÷ 100

Quantity of Colloidal Silicon Dioxide, NF

Quantity of Colloidal Silicon Dioxide, NF = (1.425 kg x % yield) ÷ 100

Quantity of Lactose Monohydrate, #316, Fast Flo, NF

Quantity of Lactose Monohydrate, #316, Fast Flo, NF = (19.475 kg x % yield) ÷ 100

| Lot Number | Strength mg | Minocycline Potency as is % | Adjusted Minocycline HCl kg | Adjusted Intragranular Lactose Monohydrate kg | Amount of Hypromellose kg | Total Intragranular Net Weight kg | Intragranular Yield kg | Adjusted Lactose Monohydrate kg | Adjusted Colloidal Silicon Dioxide kg | Adjusted Magnesium Stearate kg |
|---|---|---|---|---|---|---|---|---|---|---|
| 7K3367 | 65 | 84.3 | 36.625 | 78.325 | 51.3 | 166.25 | 98.1 | 19.105 | 1.398 | 2.796 |
| 7L3455 | 65 | 83.8 | 36.844 | 78.106 | 51.3 | 165.25 | 98.6 | 19.202 | 1.405 | 2.81 |
| 7L3456 | 65 | 83.8 | 36.844 | 78.106 | 51.3 | 166.25 | 99 | 19.28 | 1.411 | 2.822 |
| 7K3411 | 115 | 83.9 | 65.107 | 49.84 | 51.3 | 166.25 | 97.9 | 19.066 | 1.395 | 2.79 |
| 7L3457 | 115 | 83.9 | 62.97 | 49.84 | 51.3 | 166.25 | 98.6 | 19.124 | 1.399 | 2.799 |
|  |  | 83.7 | 2.142 |  |  |  |  |  |  |  |
| 7L3478 |  | 83.7 | 65.623 | 49.76 | 51.3 | 166.25 | 98.6 | 19.202 | 1.405 | 2.81 |

Commercial 115 mg Batches - Launch Qty

| | | | | | | | | | | |
|---|---|---|---|---|---|---|---|---|---|---|
| 8J4549 | 115 | 84.8 | 64.416 | 50.53 | 51.3 | 166.25 | 100 | 19.475 | 1.425 | 2.85 |
| 8J4548 | 115 | 84.8 | 64.416 | 50.53 | 51.3 | 166.25 | 100 | 19.475 | 1.425 | 2.85 |
| 8J4547 | 115 | 84.8 | 64.416 | 50.53 | 51.3 | 166.25 | 100 | 19.475 | 1.425 | 2.85 |
| 8J4546 | 115 | 85.1 | 10.79 | 50.57 | 51.3 | 166.25 | 99.9 | 19.456 | 1.424 | 2.847 |
|  |  | 84.8 | 53.588 |  |  |  |  |  |  |  |
|  |  | total Mino: | 64.378 |  |  |  |  |  |  |  |
| 8J4545 | 115 | 85.1 | 64.189 | 50.761 | 51.3 | 166.25 | 99.9 | 19.456 | 1.424 | 2.847 |
| mean |  | 84.9 | 64.3655 | 50.5842 | 51.3 | 166.25 | 99.9 | 19.456 | 1.4246 | 2.8488 |
| SD |  | 0.155 | 0.8845 | 0.100340421 | 0 | 0 | 0.054772256 | 0.001046729 | 0.000547723 | 0.001643168 |
| theoretical QTY |  |  | 54.625 kg | 60.325 kg | 51.3 kg | 166.25 kg | 100 | 19.475 kg | 1.425 kg | 2.850 kg |

FIG 1A

Commercial 65 mg Batches - Launch Qty

| | | | | | | | | |
|---|---|---|---|---|---|---|---|---|
| 8J4506 | 65 | 85.1 | 38.281 | 78.67 | 51.3 | 166.25 | 100 | 19.475 | 1.425 | 2.85 |
| 8J4507 | 65 | 85.1 | 38.281 | 78.67 | 51.3 | 166.25 | 98.8 | 19.241 | 1.408 | 2.816 |
| 8J4512 | 65 | 84.8 | 19.9 | 78.54 | 51.3 | 166.25 | 100 | 19.475 | 1.425 | 2.85 |
| | | 84.8 | 18.509 | | | | | | | |
| | | total Modo: | 38.409 | | | | | | | |
| 8J4510 | 65 | 84.8 | 36.409 | 78.54 | 51.3 | 166.25 | 100 | 19.475 | 1.425 | 2.85 |
| 8J4509 | 65 | 84.8 | 36.409 | 78.54 | 51.3 | 166.25 | 100 | 19.475 | 1.425 | 2.85 |
| 8J4508 | 65 | 84.8 | 36.409 | 78.54 | 51.3 | 166.25 | 99.6 | 19.397 | 1.419 | 2.839 |
| 8J4511 | 65 | 84.8 | 36.409 | 78.54 | 51.3 | 166.25 | 100 | 19.745 | 1.425 | 2.85 |
| mean | | 84.86 | 36.372 | 78.57714286 | 51.3 | 165.25 | 99.77142857 | 19.468 | 1.421714286 | 2.843571429 |
| SD | | 0.138873015 | 0.062 | 0.063433505 | 0 | 0 | 0.453857368 | 0.149157835 | 0.006447591 | 0.012830395 |
| theoretical QTY | | | 36.975 kg | 84.075 kg | 51.3 | 166.25 kg | 100 | 19.475 kg | 1.425 kg | 2.850 kg |

All 65 mg Data

| | | | | | | | | | | |
|---|---|---|---|---|---|---|---|---|---|---|
| 7K3367 | 65 | 84.3 | 36.625 | 78.325 | 51.3 | 166.25 | 98.1 | 19.105 | 1.398 | 2.796 |
| 7L3455 | 65 | 83.8 | 36.844 | 78.106 | 51.3 | 166.25 | 98.6 | 19.202 | 1.405 | 2.81 |
| 7L3456 | 65 | 83.8 | 36.844 | 78.106 | 51.3 | 166.25 | 99 | 19.28 | 1.411 | 2.822 |
| 8J4506 | 65 | 85.1 | 36.281 | 78.67 | 51.3 | 166.25 | 100 | 19.475 | 1.425 | 2.85 |
| 8J4507 | 65 | 85.1 | 38.281 | 78.67 | 51.3 | 166.25 | 98.8 | 19.241 | 1.408 | 2.816 |
| 8J4512 | 65 | 84.8 | 36.409 | 78.54 | 51.3 | 166.25 | 100 | 19.475 | 1.425 | 2.85 |
| 8J4510 | 65 | 84.8 | 36.409 | 78.54 | 51.3 | 166.25 | 100 | 19.475 | 1.425 | 2.85 |
| 8J4509 | 65 | 84.8 | 36.409 | 78.54 | 51.3 | 166.25 | 100 | 19.475 | 1.425 | 2.85 |
| 8J4508 | 65 | 84.8 | 36.409 | 78.54 | 51.3 | 166.25 | 99.6 | 19.397 | 1.419 | 2.839 |
| 8J4511 | 65 | 84.8 | 36.409 | 78.54 | 51.3 | 166.25 | 100 | 19.475 | 1.425 | 2.85 |
| mean | | 84.61 | 36.492 | 78.4577 | 51.3 | 166.25 | 99.41 | 19.36 | 1.4166 | 2.8333 |
| SD | | 0.479457297 | 0.207898527 | 0.207900644 | 0 | 0 | 0.721603297 | 0.140653868 | 0.010243697 | 0.020515848 |
| theoretical QTY | | | 54.625 | 80.325 | 51.3 | 166.25 kg | 100 | 19.475 kg | 1.425 kg | 2.850 kg |

| | min | 51.3 | 166.25 | 98.1 | 19.105 | 1.398 | 2.796 |
|---|---|---|---|---|---|---|---|
| | max | 51.3 | 166.25 | 100 | 19.475 | 1.425 | 2.85 |
| | % | 100% | 100% | 98.1 - 100% | 98.1 - 100 | 98.1 - 100 | 98.1 - 100 |

FIG. 1B

All 115 mg Data

| | | | | | | | | | |
|---|---|---|---|---|---|---|---|---|---|
| 7K3441 | 115 | 83.9 | 85.107 | 49.84 | 51.3 | 166.25 | 97.9 | 19.066 | 1.395 | 2.79 |
| 7L3457 | 115 | 83.9 | 85.112 | 49.84 | 51.3 | 166.25 | 98.6 | 19.124 | 1.399 | 2.799 |
| 7L3478 | 115 | 83.8 | 65.190 | 49.76 | 51.3 | 166.25 | 98.5 | 19.202 | 1.405 | 2.81 |
| 8J4549 | 115 | 84.6 | 64.416 | 50.53 | 51.3 | 166.25 | 100 | 19.475 | 1.425 | 2.85 |
| 8J4548 | 115 | 84.6 | 64.416 | 50.53 | 51.3 | 166.25 | 100 | 19.475 | 1.425 | 2.85 |
| 8J4547 | 115 | 84.8 | 64.416 | 50.53 | 51.3 | 166.25 | 100 | 19.475 | 1.425 | 2.85 |
| 8J4546 | 115 | 85.1 | 64.378 | 50.57 | 51.3 | 166.25 | 99.9 | 19.456 | 1.424 | 2.847 |
| 8J4545 | 115 | 85.1 | 64.189 | 50.761 | 51.3 | 166.25 | 99.9 | 19.456 | 1.424 | 2.847 |
| mean | | 84.5125 | 64.707125 | 50.295125 | 51.3 | 166.25 | 99.3625 | 19.341125 | 1.41525 | 2.830376 |
| SD | | 0.579254447 | 0.506620279 | 0.405857447 | 0 | 0 | 0.85345934 7 | 0.178226531 | 0.013188198 | 0.026016135 |
| theoretical QTY | | | 54.625 | 60.325 | 51.3 | 166.25 kg | 100 | 19.475 kg | 1.425 kg | 2.850 kg |

| | min | 51.3 | 166.25 | 97.9 | 19.066 | 1.395 | 2.79 |
|---|---|---|---|---|---|---|---|
| | max | 51.3 | 166.25 | 100 | 19.475 | 1.425 | 2.85 |
| | % | 100% | 100% | 97.9 - 100 | 97.9 - 100 | 97.9 - 100 | 97.9 - 100 |

METHOD FOR THE TREATMENT OF ACNE AND CERTAIN DOSAGE FORMS THEREOF

CROSS REFERENCE TO RELATED APPLICATIONS

This application claims the benefit of U.S. Provisional Application Ser. No. 61/086,728, filed Aug. 6, 2008, the contents of which are incorporated by reference herein. This application also claims the benefit of U.S. Provisional Application Ser. No. 61/210,882, filed Mar. 23, 2009, the contents of which are incorporated by reference herein.

BACKGROUND OF THE INVENTION

1. Field of the Invention

The present disclosure relates to certain low dose forms of weight-based dosing of minocycline, preferably minocycline hydrochloride, in a slow, continuous or extended release delivery vehicle to form oral dosage units that provide for the effective treatment of acne with reduced or almost negligible side effects. The present disclosure also relates to the method for treating acne with reduced or almost negligible side effects by the use of such dosage forms based on a person's weight.

2. Description of the Related Art

Acne affects large patient populations, and is a common inflammatory skin disorder that usually localizes in sebaceous areas of the body, including on the face, back and chest.

Oral tetracycline-class antibiotics are frequently used in the treatment of acne. Tetracycline-class antibiotics are known to have some side effects. These side effects include vestibular side effects or symptoms such as vertigo, dizziness or blurred vision. These effects are sometimes disabling. See, Gould & Brookler, Arch. Otolarang. Vol. 96, p. 291 (1972); Williams et al., Lancet, Sep. 28, 1974, p. 144-45; Fanning & Gump, Arch. Intern. Med., Vol. 136, pp. 761-62 (1976). Headache and general malaise, along with gastrointestinal symptoms such as the diarrhea, nausea, gas, or cramps, may also occur. Dry nose and dry mouth are also occasionally encountered.

One oral tetracycline-class antibiotic used in the treatment of acne is minocycline hydrochloride. Oral dosage forms of minocycline hydrochloride are available commercially under various trade names.

The dosing schedule used most frequently for treating acne using currently available immediate-release oral dosage forms is 100 mg of minocycline (free base equivalent) administered twice daily, see Leyden, J. Cutis 2006; 78 (suppl 4):4-5. However, some patients experience adverse effects with currently available immediate-release oral dosage forms, leading to reduced rates of patient compliance. See Stewart, M. et al., Cutis 2006; 78 (suppl 4):11-20.

Although the development of slowly dissolving forms of minocycline hydrochloride was a significant advance in the art, there remains a long-felt need for treatments that are effective in suppressing acne but are associated with fewer adverse effects than those associated with the various oral dosage forms of minocycline hydrochloride. Such a need is addressed in the present assignees corresponding pending applications that address weight based dosing, as well as certain commercial 45/90/135 mg dose forms.

SUMMARY OF THE INVENTION

According to the present disclosure, a method is provided for the treatment of acne in which a low, but antibiotically effective, dose of minocycline, preferably minocycline hydrochloride, in a slow, continuous or extended release delivery vehicle at a release rate that provides a steady amount, without an initial loading dose, in the patient/person over a prolonged period of time. This dosage units or strengths of the present disclosure are 65 mg or 115 mg, and are selected to provide the patient with preferably certain body weights and with as close as possible to 1 milligram per kilogram of body weight (1 mg/kg) of the minocycline. This dosing method produces effective acne treatment, and far fewer side effects.

The present disclosure includes oral dosage units or strengths that are either 65 mg or 115 mg. The oral dosage form includes minocycline, preferably minocycline hydrochloride, and has a slow, continuous or extended release delivery vehicle with a desired release rate that provides a constant amount, without an initial loading dose, in the patient over an extended period of time. The selection of either the 65 mg or 115 mg dosage strength is based, in great part, on the body weight of the patient in order to provide the patient with as close as possible to 1 mg/kg/day of the minocycline.

BRIEF DESCRIPTION OF THE SEVERAL VIEWS OF THE DRAWINGS

FIGS. 1A-1C are a table showing batch records for 65 mg and 115 mg oral dosage forms according to the present disclosure.

DETAILED DESCRIPTION OF THE INVENTION

The present disclosure is directed to a 65 mg and a 115 mg oral dosage unit or strength for the treatment of acne. Each dosage strength includes minocycline, preferably minocycline hydrochloride, in a dissolution rate controlling matrix polymer, which optimizes the temporal release from the dosage strength to deliver therapeutic amounts, when orally administered. Each dosage strength, namely 65 mg and 115 mg, describes a therapeutic dosage strength of minocycline incorporated therein. The dosage strengths are calculated based on the therapeutic concentrations required per day; on the basis of patient/person weight, which concentrations amount to about 1 mg/kg/day. For purposes of the present disclosure, "about 1 mg/kg of body weight per day" means from 0.84 mg/kg/day to 1.24 mg/kg/day. The dissolution profiles, and/or bioequivalence studies, which are generated from the 65 mg and 115 mg dosage strengths, support the fact that there are therapeutic levels of the minocycline in vivo. Each dosage strength is to be administered once a day. Each dosage strength provides, without an initial load dose, a relatively if not completely constant, slow, continuous release of the minocycline from the dosage strength in the patient so that therapeutic efficacy for an extended period of time, namely for at least twelve (12) hours, is received by the patient. This is evident from the in vitro dissolution data in a pH of 1.2, which demonstrates a desired, constant release rate of the minocycline of: 35% to 50% within 1 hour; 60% to 75% in 2 hours, and at least 90% in 4 hours. For these dosage forms, the preferably desired mean value is 38% to 43% within 1 hour; 66% to 70% in 2 hours, and, of course, at least 90% in 4 hours.

Dissolution testing, which was conducted according to the approved test method using the currently approved media (0.1N HCl, pH 1.2), of the 65 mg and the 115 mg dosage strengths have found the following release rates +/−0.50%:

| Time in hours | 65 mg (8.9% ± 0.2% HP Substitution in HPMC) | 115 mg (8.9% ± 0.2% HP Substitution in HPMC) |
| --- | --- | --- |
| 1 | 41% | 39% |
| 2 | 68% | 68% |
| 3 | 90% | 89% |
| 4 | at least 90%; about 100% | at least 90%; about 100% |

Extrapolating from data collected from 45 mg and 90 mg NDA and commercial manufacturing data, dissolution testing using the currently approved media (0.1 HCl, pH 1.2), of the 65 mg and 115 mg manufactured utilizing Methocel EV50 Premium LV with an 8.3-8.7% HP substitution would have the following release rates +/−0.50%:

| Time in hours | 65 mg (8.3-8.7% HP Substitution in HPMC) | 115 mg (8.3-8.7% HP Substitution in HPMC) |
| --- | --- | --- |
| 1 | 37% | 40% |
| 2 | 61% | 70% |
| 3 | 90% | 89% |
| 4 | at least 90%; about 100% | at least 90; about 100% |

The dosage unit can be a capsule, tablet, or caplet. It is believed that the course of treatment with either the 65 mg or 115 mg dosage unit typically lasts 12 weeks.

The preferred formulations for the 65 mg and 115 mg dosage units, that preferably are tablets, are set forth below:

| Component | 65 mg dosage unit mg/dose | 115 mg dosage unit mg/dose |
| --- | --- | --- |
| Minocycline Hydrochloride Non Sterile (USP) - anhydrous base | 65 | 115 |
| Lactose Monohydrate - intragranular | 177 | 127 |
| Lactose Monohydrate - extragranular | 41 | 41 |
| Hypromellose Type 2910 (Methocel E50 Premium LV) (USP) | 108 | 108 |
| Colloidal Silicon Dioxide | 3 | 3 |
| Magnesium Stearate (Impalpable Powder) FCC HyQual Product Code 2255 | 6 | 6 |
| Purified Water, USP (Eliminated during Drying) | — | — |
| Core Total Weight: | 400 | 400 |
| Opadry II Blue | 14 | |
| Opadry II Green | | 12 |
| Purified Water, USP (Eliminated during Coating) | | |
| Carnauba Wax (not part of the unit dose formula) | Trace | Trace |
| Coated Total Weight: | 414 | 412 |

As noted above, the 65 mg dosage form contains Opadry II Blue. Opadry II Blue contains: hypromellose type 2910 USP, lactose monohydrate NF, titanium dioxide USP, polyethylene glycol 3350 NF, FD&C Blue #1, FD&C Blue #2, D&C Yellow #10, and triacetin USP. The amount of hypromellose is between 29% to 51% w/w, and the amount of lactose monohydrate is between 15% to 27% w/w of the coating.

The 115 mg dosage form, as noted above, contains Opadry II Green. Opadry II Green contains: hypromellose type 2910 USP, lactose monohydrate NF, titanium dioxide USP, D&C yellow #10, FD&C Blue #1, FD&C Blue #2, and triacetin USP. The amount of hypromellose is between 29% to 51% w/w, and the amount of lactose monohydrate is between 20% to 36% w/w of the coating.

Because of the variations in body weight encountered in clinical practice, in the actual practice of the present disclosure, it is not practical to provide every patient with exactly 1 mg/kg/day of minocycline. However, it is acceptable to approximate this dose by providing the patient with about 1 mg/kg/day. For the 65 mg dose unit or tablet strength, the actual mg/kg/day dose, or the about 1 mg/kg/day, is between 0.84 mg/kg/day to 1.24 mg/kg/day, and in the preferred body weight range of the patient set forth below, between 0.84 mg/kg/day to 1.18 mg/kg/day. For 115 mg, the actual mg/kg/day dose, or the about 1 mg/kg/day, is between 0.92 mg/kg/day to 1.12 mg/kg/day.

For each dosage unit, the lactose monohydrate, both intragranular and extragranular, is a filler that is a fast dissolving carrier. The preferred lactose monohydrate is sold under the name #316 Fast Flo. The hypromellose is a slow dissolving binder/release rate control polymer or carrier. The hypromellose has a low viscosity, namely between 40 cps and 60 cps. The preferred hypromellose is sold under the name Hypromellose Type 2910 (Methocel E50 Premium LV).

The intragranular lactose monohydrate is an intragranular fast dissolving carrier, and the hypromellose is a slow dissolving carrier. The minocycline, the intragranular lactose monohydrate and the hypromellose or slow dissolving carrier form the intragranular granules or intragranular component of each dosage strength. The extragranular lactose monohydrate or extragranular fast dissolving carrier, colloidal silicon dioxide, and magnesium stearate form the extragranular component of each dosage strength. As described below, the intragranular components are blended together. The extragranular lactose monohydrate or fast dissolving carrier completely encapsulates or coats the intragranular granules. The ratio of extragranular fast dissolving carrier to slow dissolving carrier assists in defining a dissolution profile that enables once-a-day dosing in accordance with the present disclosure. It is advantageous to formulate the dosage forms so that the ratio of the extragranular fast dissolving carrier to slow dissolving carrier is from 0.30 to 0.50, and preferably from 0.35 to 0.45, with about 0.36 to 0.40 being particularly preferable.

The fast dissolving carrier, whether intragranular or extragranular, is any filler, binder, vehicle, or excipient that quickly dissolves in an aqueous physiological medium, such as gastric fluid, thereby tending to quickly release the active ingredient, namely minocycline hydrochloride. Besides the preferred lactose monohydrate, lactose, its salts and hydrates can also be used for the fast dissolving carrier.

The slow dissolving carrier is a binder, vehicle, or excipient that dissolves slowly over the course of hours and perhaps a day, thereby slowing the release of the active ingredient. Besides the preferred hypromellose or hydroxypropylmethyl cellulose, examples of other slow dissolving carriers that can be used are polyvinyl pyrrolidone, polyvinyl acetate, microcrystalline cellulose, methyl cellulose, ethyl cellulose, or hydroxypropyl cellulose.

The magnesium stearate is a lubricant, and the colloidal silicon dioxide is a glidant. These ingredients are used to facilitate processing of each dosage strength.

Significantly for each dosage unit, the total amount of the core tablet is 400 mg. In addition, to insure the desired release rates set forth above for both the 65 mg and 115 mg dosage strengths, the slow dissolving carrier preferably remains constant at about 27% (namely 108 mg) of the total core weight (namely 400 mg) of the dosage strength. The term "about" for the hypromellose means + or −1%.

The preferred coating solution system used is Opadry II Series 85G, blue for the 65 mg and green for the 115 mg. This coat contains up to 51% w/w hypromellose/HPMC. It has now been found that by varying the coating weight, one may fine tune the dissolution profile. The 115 mg dosage strength because of its high active to polymer ratio necessitates a thinner coating (wet target 3.3%, dry target 3.1%), with a dry range of 3.0 to 3.3% to achieve the desired 1 and 2 hour dissolution time points. Conversely, the 65 mg dosage strength requires a thicker coating (wet target 3.85%, dry target 3.5%), with a dry range of 3.5 to 4.0% because of its lower active to polymer ratio to achieve the desired 1 hour dissolution time point. Thus, these coatings provide a secondary matrix forming polymer barrier to fine tune/adjust the desired dissolution profile.

As noted above, the 65 mg or the 115 mg dosage unit should be selected based on the body weight of the patient. It is recommended that the following body weight of the patient be considered when selecting the dosage (tablet) strength.

| Patient's Weight (lbs.) | Patient's Weight (kg) | Tablet Strength (mg) | Actual mg/kg Dose |
|---|---|---|---|
| 121-170 (preferred) | 55-77 | 65 | 1.18-0.84 |
| 115-170 | 52-77 | 65 | 1.24-0.84 |
| 226-276 | 103-125 | 115 | 1.12-0.92 |

The first (preferred) patient's weight range for the 65 mg dosage unit is preferred, however for the weight range of 115 lbs to 121 lbs, 65 mg dosage strength can be used but provides an actual mg/kg dose in the patient that can be as much as 1.24 mg/kg instead of 1.18 mg/kg.

Due to the release rates set forth above, the minocycline in the 65 mg and 115 mg dosage strengths is released slowly and continuously so that only once-a-day, or once daily, dosing is needed.

These dosage strengths release the minocycline hydrochloride such that the maximum blood concentration of the minocycline hydrochloride ($C_{max}$) is reached at 3.5 hours to 4.0 hours after administration (Tmax).

The side effects, including vestibular, that are virtually eliminated as compared to placebo, include: headache, fatigue, dizziness, drowsiness, pruritus, lightheadedness, malaise, mood alteration, somnolence, urticaria, tinnitus, arthralgia, vertigo, dry mouth, and myalgia. Other adverse effects that are avoided are: blood/lymphatic system, ear and labyrinth, endocrine, eye, gastrointestinal, immune system, syncope, contusions, vaginal itching, nausea, nasal congestion, cough, itch, rash, stomach pain, infections, infestations, laboratory blood abnormalities, metabolism, nutrition, musculoskeletal and connective neoplasms, benign, malignant and unspecified nervous system psychiatric, renal and urinary, reproductive system, breast disorders, respiratory, thoracic and mediastinal, skin and subcutaneous tissue, and vascular.

Figure 1:
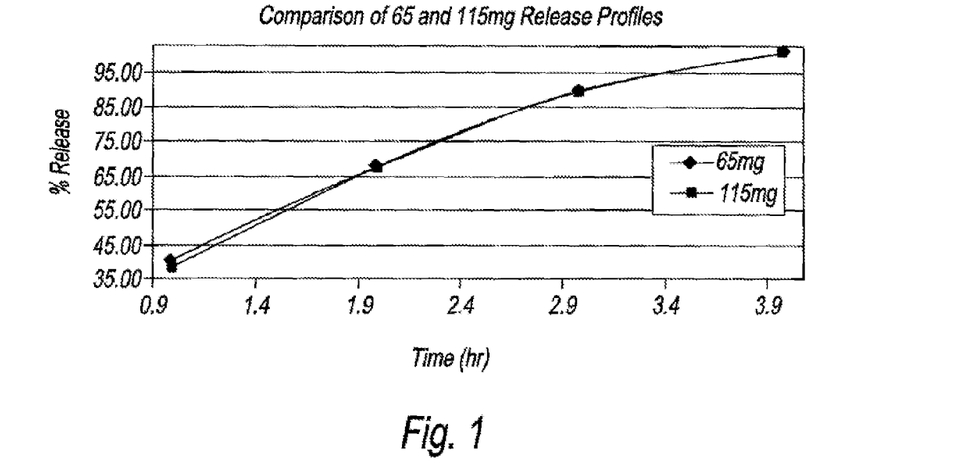
FIG. 1 is a comparison of 65 and 115 mg release profiles.
Figure 2:
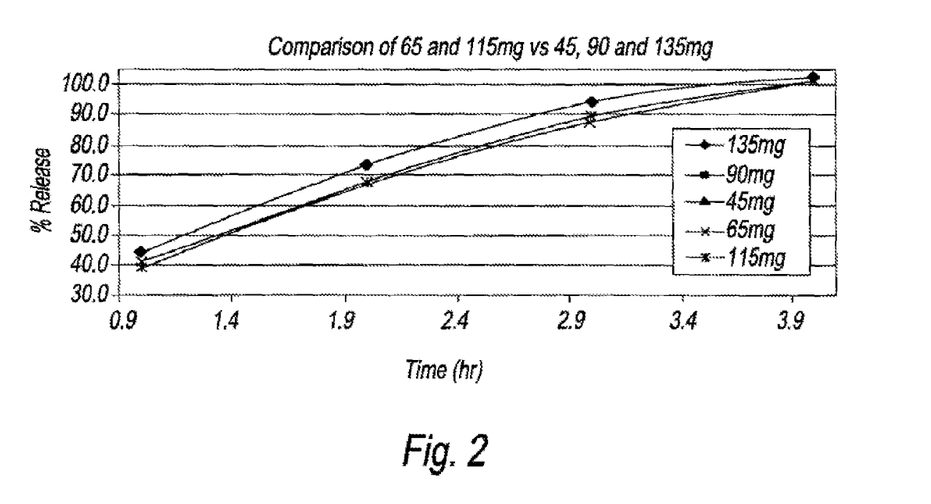
FIG. 2 is a comparison of 65 and 115 mg to 45, 90, and 135 mg.

A Similarity Comparison was made between the dissolution profiles of the 65 and 115 mg dosage strengths. A comparison was also performed between the 65 and 115 mg dosage strengths, and 45 and 90 mgs dosage strengths. The results (Table 1) show that the 65 and 115 mg dosage strengths are statistically similar to each other ($f_2$ greater than 50%). The release profiles are compared graphically in FIG. 1. The similarity comparison of the 65 and 115 mg dosage strengths to the current 45 mg, and 90 mg dosage strengths also shows that the release profiles are statistically comparable. The release profiles of all four dosage strengths, as well as 135 mg dosage strength, are compared graphically in FIG. 2. All dissolution testing was conducted according to the approved test method using the currently approved media, namely 0.1N HCl, pH 1.2.

TABLE 1

Similarity Comparison of 65 and 115 mg dosage strengths

| Strength (mg) | Similarity Factor ($f_2$) Spec ≥ 50% |
|---|---|
| 65 vs. 115 | 93 |
| 65 vs. 45 | 86 |
| 65 vs. 90 | 90 |
| 115 vs. 45 | 88 |
| 115 vs. 90 | 91 |

Figure 3:
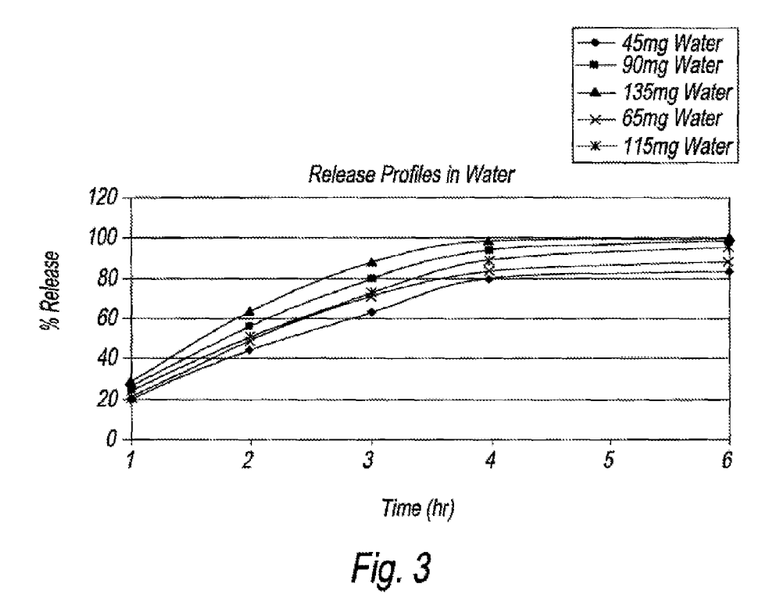
FIG. 3 is a comparison of dissolution profiles in water.

While all of the dissolution testing discussed above has been according to the approved test method using the currently approved media (0.1 N HCl, pH 1.2), dissolution testing has been conducted in water. A comparison of dissolution profiles in water for all five dosage strengths noted above is shown in FIG. 3.

The 65 mg and 115 mg dosage strengths are made by the similar process. The batch size is 190 kg that equates to 475,000 tablets.

A 60 liter pressure vessel is calibrated using purified water to achieve a spray rate of 7,500 ml/minute+/−500 ml/min. 56.524 kg of purified water is added to the 60 L pressure vessel. The intragranular lactose monohydrate is de-agglomerated through a comminuting mill. To a high shear granulator, add in the following sequence, hypromellose, adjusted minocycline hydrochloride (adjusted based on assay and water content and adjusted to a maximum amount of 15% of the minocycline) spread evenly over the surface of the hypromellose, and the de-agglomerated intragranular lactose monohydrate (that maybe adjusted based on the adjusted minocycline hydrochloride). Dry blend the contents of the high shear granulator using only the impeller for 2 minutes+/−10 seconds.

Spray the contents of the 60 L pressure vessel into the high shear granulator set with impeller and chopper on. Spray to completion in 7 minutes, 34 seconds+/−30 seconds.

Wet mass the contents of the high shear granulator using the impeller and chopper for 3 minutes+/−30 seconds. Discharge the contents of the high shear granulator through a comminuting mill and collect in a poly-lined drum.

Transfer the wet milled granulation to the pre-warmed fluid bed drier. Dry the contents of the fluid bed drier with an inlet temperature of 60-70 C to a moisture level (% LOD) of 1.2%-2.2% (target 1.8%) for the 65 mg strength and 1.8-2.8% (target 2.2%) for the 115 mg strength.

Pass the dried granulation through a comminuting mill to size the granules and collect in a poly-lined drum. Calculate the yield of the dried milled granulation and adjust the weight of extragranular excipients. Transfer the dried milled granulation to a Tote.

Add the adjusted extragranular lactose monohydrate and adjusted colloidal silicon dioxide to a V blender and blend for 2 minutes+/−15 seconds. Pass this blend through a comminuting mill and collect in a poly-lined drum. Add this blend to the Tote. Blend the contents of the Tote for 10 minutes+/−30 seconds.

Remove approximately 5 kg of this blend and add to a polyethylene bag containing the adjusted magnesium stearate and mix the contents by hand. Add this blend to a V blender and blend for 50 revolutions. Pass this blend through a comminuting mill and collect in a poly-lined drum. Add this blend to the Tote.

Blend the contents of the tote for 2 minutes+/−30 seconds. Discharge the contents of the Tote into poly-lined drums.

Compress the blend utilizing a rotary tablet press to a target tablet weight of 400 mg (390-410 mg), with a hardness of 15 kp (12-18 kp). Pass the compressed tablets through a tablet de-duster and a metal detector; collect the tablets in a poly-lined drum.

Coat the tablets in a film coater with a solution of 18% solids Opadry II Series G Blue (65 mg) or Opadry II Series G Green (115 mg). The coating solution will be sprayed at a spray rate of 400 mg/min (300 mg/min-500 mg/min) at an inlet temperature of 62 C (range 60-70 C) until a wet coat weight of 3.3% for 115 mg tablet or 3.85% for the 65 mg tablet has been achieved. Dry the tablets with an inlet temperature of 62 C (range 60-70 C) for 2 minutes. For the 65 mg tablet, theoretical dry weight gain is 3.5% (range 3.5-4.0%), for the 115 mg tablet, theoretical dry weight gain is 3.1% (range 3.0-3.3%). Cool the tablets to NMT 35 C.

Polish the tablets by adding Carnauba Wax and tumble for 2 minutes. Transfer the coated tablets to poly-lined containers.

To summarize some criteria for manufacturing of these dosage strengths, note the following:

|  | 65 mg mg/dose | 115 mg mg/dose |
|---|---|---|
| Intragranular Component Dry Blend Parameters: Screening of intragranular Lactose Monohydrate: | | |
| Spacer: | 0.150" | 0.150" |
| Speed: | approx. 875 rpm | approx. 875 rpm |
| Impeller Seal Pressure | 10 +/− 5 psi | 10 +/− 5 psi |
| Chopper Seal Pressure | 10 +/− 5 psi | 10 +/− 5 psi |
| Mixing Time | 2 minutes +/− 10 sec. | 2 minutes +/− 10 sec. |
| Granulation Parameters: | | |
| Granulation Spray Rate | 7,500 g/min +/− 500 g/min | |
| Granulation Time | 7 min. 34 sec +/− 30 seconds | |
| Wet Massing Parameters | | |
| Mixing Time | 3 minutes +/− 30 seconds | |
| Wet Milling Parameters | | |
| Spacer: | 0.150" | 0.150" |
| Speed: | approx. 900 rpm | approx. 900 rpm |
| Fluid Bed Drying Parameters | | |
| Pre-heat - Fluid Bed Dryer | | |
| Process Air Volume Set Point | 500-1000 cfm | 500-1000 cfm |
| Inlet Air Temperature | 65 C. (60-70 C.) | 65 C. (60-70 C.) |
| Drying Parameters | | |
| Initial Process Air Volume Set Point | 1200 cfm | 1200 cfm |
| Process Air Volume Set Point Range | 500-2500 cfm | 500-2500 cfm |
| Inlet Air Temperature | 65 C. | 65 C. |
| Set Point Range | (60-70 C.) | (60-70 C.) |
| Shake Interval | 30 seconds | 30 seconds |
| Shake Duration | 5 seconds | 5 seconds |
| Dry Sizing Parameters | | |
| Feed Screw Speed | 14-16 rpm | 14-16 rpm |
| Rotor Speed | 4600 +/− 25 rpm | 4600 +/− 25 rpm |
| Extragranular Component Excipient Blending/Milling Parameters: Adjusted Colloidal Silicon Dioxide, NF + extragranular Lactose form extragranular blend | | |
| A & M 3 cu. Ft. V-Blender Speed: | 2 minutes +/− 15 seconds | |
| Spacer: | 0.150" | 0.150" |
| Speed: | approx. 875 rpm | approx. 875 rpm |
| Blending of the intragranular and extragranular blends | | |
| Bin Speed | 15 rpm | 15 rpm |
| Bin Blend Time | 10 minutes +/− 15 sec | 10 minutes +/− 15 sec |
| Adjusted Magnesium Stearate + 5 kg Blend | | |
| PK 1 Cu. Ft. V-Blender Speed: | 2 minutes +/− 15 seconds | |
| Spacer: | 0.150" | 0.150" |
| Speed: | approx. 875 rpm | approx. 875 rpm |
| Final Blend Parameters | | |
| Bin Speed | 15 rpm | 15 rpm |
| Bin Blend Time | 10 minutes +/− 15 sec | 10 minutes +/− 15 sec |

-continued

|  | 65 mg mg/dose | 115 mg mg/dose |
|---|---|---|
| Compression Parameters |  |  |
| Size: | 0.2343 × 0.6250" | 0.2343 × 0.6250" |
| Tablet weight | 400 mg | 400 mg |
| Acceptance Criteria | 390 mg-410 mg (97.5-102.5%) | |
| Tablet Hardness |  |  |
| Average Hardness | 15 kp | 15 kp |
| Individual Hardness | 12-18 kp | 12-18 kp |
| Tablet Thickness |  |  |
| Target | 4.52 mm | 4.52 mm |
| Range | For Information Only | For Information Only |
| Coating Parameters: |  |  |
| Coating Suspension Parameters |  |  |
| Mixing Time | NLT 60 minutes | NLT 60 minutes |
| Screen Coating Suspension Prior to Use | 80 mesh ss screen | 80 mesh ss screen |
| Coating Parameters |  |  |
| Proposed % weight gain - Target | 3.85% wet | 3.3% wet |
| Proposed % weight gain - Range | 3.0-4.0% | 3.0-3.3% |
| Post spraying parameters (drying) |  |  |
| Supply Air Temperature | 62 C. (50-70 C.) | 62 C. (50-70 C.) |
| Pan Speed | 7 +/− 2 rpm | 7 +/− 2 rpm |
| Post Drying parameters |  |  |
| Supply Air Temperature | cool to <35 C. | cool to <35 C. |

Figure 1B:
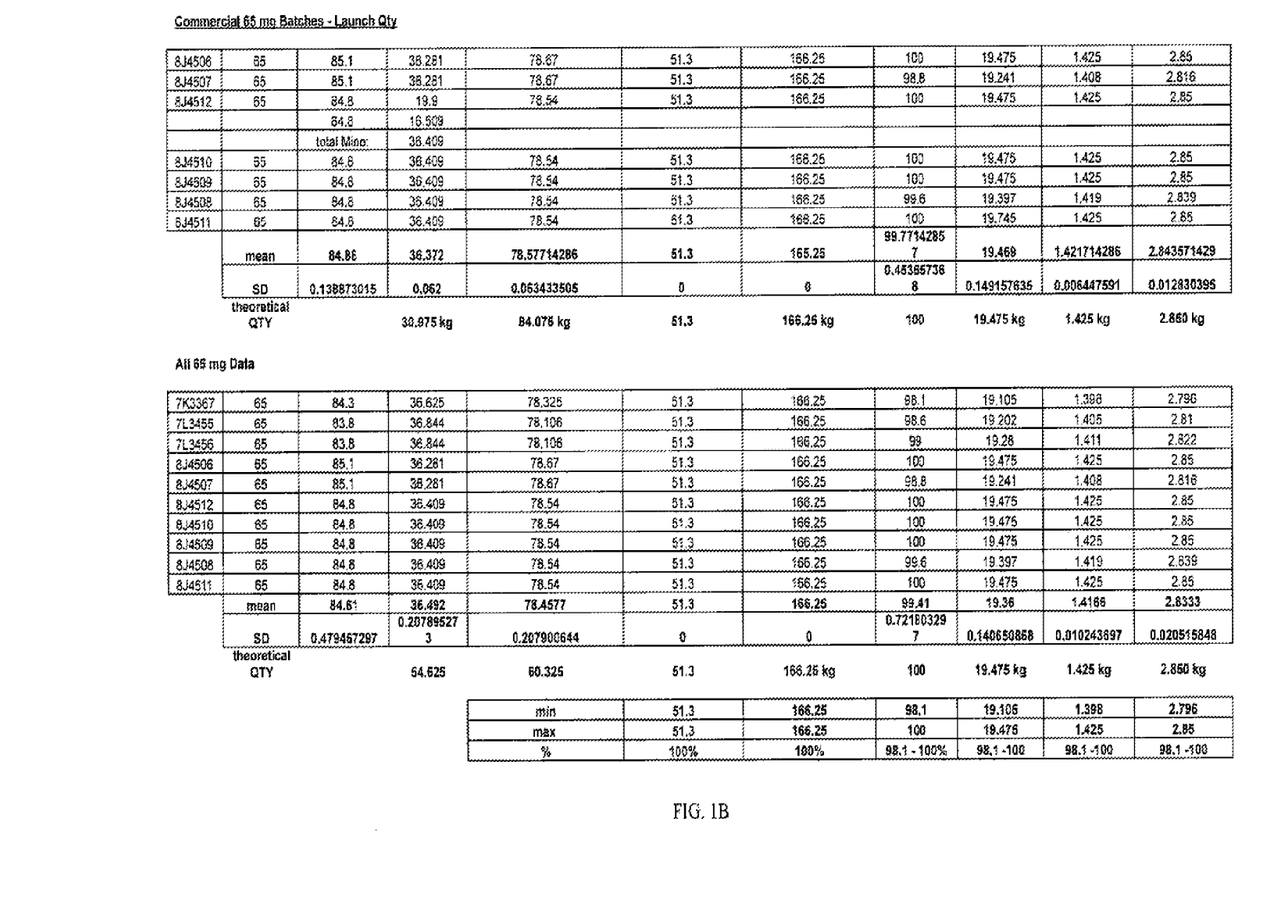
Figure 1C:
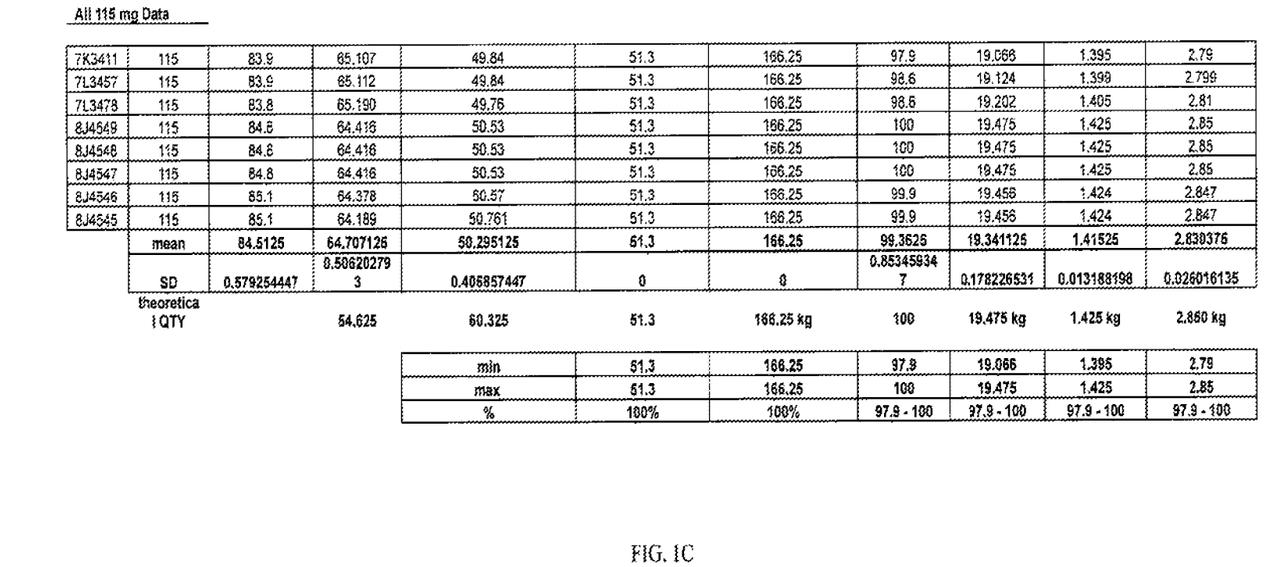

FIGS. 1A-1C are a table showing the batch records for 65 mg oral dosage forms and 115 mg oral dosage forms of the present disclosure. During the making of the dosage forms using the batch process discussed above, it has been found that the potency of the minocycline decreases below one hundred percent. A decrease in the potency of minocycline requires the batch to receive an increase in the amount of minocycline so that the resulting potency of the minocycline in each dosage form has 100 percent potency for the stated amount of minocycline in the dosage form. For each dosage form, the intragranular components are the minocycline, the intragranular lactose monohydrate, and the Hypromellose. The Hypromellose always remains constant. Consequently, the amount of intragranular lactose monohydrate in the dosage form is decreased to virtually offset the increase in the amount of minocycline used.

For example, the mean value for the potency of minocycline in the 65 mg batches was 84.61%. The content of the intragranular lactose monohydrate was decreased to a minimum of 136 mg per tablet, an approximately 23.2% decrease. In addition, there was a resulting adjustment to the amounts of the extragranular components. The slight adjustment is due to the resulting intragranular yield. As shown, the 65 mg batches showed a mean intragranular yield of 98.1%. Thus, the extragranular components were adjusted accordingly.

The Table also shows the batch records for 115 mg oral dosage forms. As can be seen, the mean value for the potency of minocycline in the 115 mg batches was 84.51%. The content of the intragranular lactose monohydrate was decreased to a minimum of 105.9 mg per tablet, an approximately 16.6% decrease. In addition, there was a resulting adjustment to the amounts of the extragranular components. The slight adjustment is due to the resulting intragranular yield. As shown, the 115 mg batches showed a mean intragranular yield of 98.1%. Thus, the extragranular components were adjusted accordingly.

Thus, an aspect of the present disclosure provides a once daily, oral dosage strength for the treatment of acne that comprises: 65 mg or 115 mg of minocycline; and a dissolution rate controlling matrix polymer or carrier that optimizes a temporal release to deliver the minocycline, preferably the controlling matrix polymer is hypromellose. About 1 mg/kg/day of the minocycline, without an initial loading dose, is provided to a patient and at a constant release for an extended period of time. The constant release rate is 35% to 50% within 1 hour; 60% to 75% in 2 hours, and at least 90% in 4 hours.

The dosage units or strengths can be a tablet, capsule or caplet having 65 mg or 115 mg minocycline.

Another aspect of the present disclosure provides a method for treating acne that comprises selecting a dosage strength of either 65 mg or 115 mg with a view of the weight of the intended patient, and administering the selected dosage strength. As discussed above, the dosage form comprises 65 or 115 mg of minocycline and a dissolution rate controlling matrix polymer or carrier that optimizes a temporal release to deliver the minocycline. About 1 mg/kg/day of the minocycline, without an initial loading dose, is provided to a patient, and the constant release for an extended period of time, and wherein the constant release rate is 35% to 50% within 1 hour; 60% to 75% in 2 hours, and at least 90% in 4 hours.

The invention claimed is:

1. An oral dosage form, comprising:
    65 mg of minocycline;
    a first amount of lactose monohydrate present as an extragranular fast dissolving carrier and a second amount of lactose monohydrate present as an intragranular fast dissolving carrier;
    an amount of hydroxypropylmethylcellulose present as an intragranular slow dissolving carrier, wherein the hydroxypropylmethylcellulose is selected from the group consisting of hydroxypropylmethylcellulose that is 8.9%+/−0.2% hydroxypropoxylated and hydroxypropylmethylcellulose that is about 9.1% hydroxypropoxylated, wherein the hydroxypropylmethylcellulose has a viscosity of 40 cps to 60 cps;
    wherein the ratio of the extragranular fast dissolving carrier to intragranular slow dissolving carrier is from 0.30 to 0.50;

wherein the minocycline has a release rate, as measured in 0.1 N HCl, of about 37% within 1 hour, about 61% within 2 hours, and 90% within 3 hours when the hydroxypropylmethylcellulose is 8.9+/−0.2% hydroxypropoxylated, and wherein the minocycline has a release rate, as measured in 0.1 N HCl, of about 41% within 1 hour, about 68% within 2 hours, about 90% within 3 hours and about 100% within 4 hours when the hydroxypropylmethylcellulose is about 9.1% hydroxypropoxylated.

2. The oral dosage form of claim 1, further comprising a coating in an amount of 3.5% to 4.0% of the weight of the oral dosage form.

3. An oral dosage form, comprising:
115 mg of minocycline;
a first amount of lactose monohydrate present as an extragranular fast dissolving carrier and a second amount of lactose monohydrate present as an intragranular fast dissolving carrier;
an amount of hydroxypropylmethylcellulose present as an intragranular slow dissolving carrier, wherein the hydroxypropylmethylcellulose is selected from the group consisting of hydroxypropylmethylcellulose that is 8.9%+/−0.2% hydroxypropoxylated and hydroxypropylmethylcellulose that is about 9.1% hydroxypropoxylated, wherein the hydroxypropylmethylcellulose has a viscosity of 40 cps to 60 cps;
wherein the ratio of the extragranular fast dissolving carrier to intragranular slow dissolving carrier is from 0.30 to 0.50;
wherein the minocycline has a release rate, as measured in 0.1 N HCl, of about 37% within 1 hour, about 61% within 2 hours, and 90% within 3 hours when the hydroxypropylmethylcellulose is 8.9+/−0.2% hydroxypropoxylated, and
wherein the minocycline has a release rate, as measured in 0.1 N HCl, of about 41% within 1 hour, about 68% within 2 hours, about 90% within 3 hours and about 100% within 4 hours when the hydroxypropylmethylcellulose is about 9.1% hydroxypropoxylated.

4. The oral dosage form of claim 3, further comprising a coating in an amount of 3.0% to 3.3% of the weight of the oral dosage form.

\* \* \* \* \*